United States Patent
Dallenne et al.

(10) Patent No.: US 9,012,167 B2
(45) Date of Patent: Apr. 21, 2015

(54) QUICK METHOD FOR DETECTING ENZYMES AND MICROORGANISMS

(75) Inventors: Caroline Dallenne, Sainghin-en-Weppes (FR); Christine Favier, Wormhout (FR)

(73) Assignee: Bio-Rad Innovations, Marnes la Coquette (FR)

( * ) Notice: Subject to any disclaimer, the term of this patent is extended or adjusted under 35 U.S.C. 154(b) by 0 days.

(21) Appl. No.: 13/582,681

(22) PCT Filed: Mar. 1, 2011

(86) PCT No.: PCT/FR2011/050417
§ 371 (c)(1),
(2), (4) Date: Dec. 18, 2012

(87) PCT Pub. No.: WO2011/107703
PCT Pub. Date: Sep. 9, 2011

(65) Prior Publication Data
US 2013/0089883 A1    Apr. 11, 2013

(30) Foreign Application Priority Data

Mar. 1, 2010    (FR) ...................................... 10 51441

(51) Int. Cl.
*C12Q 1/34*    (2006.01)
*C12Q 1/44*    (2006.01)
*C12Q 1/04*    (2006.01)

(52) U.S. Cl.
CPC .. *C12Q 1/44* (2013.01); *C12Q 1/04* (2013.01); *C12Q 1/34* (2013.01)

(58) Field of Classification Search
USPC .......................................................... 435/18
See application file for complete search history.

(56) References Cited

U.S. PATENT DOCUMENTS

2012/0135438 A1    5/2012    Rambach

FOREIGN PATENT DOCUMENTS

FR    2 882 370 A1    8/2006
WO    WO2010/016911 A2    2/2010

OTHER PUBLICATIONS

International Search Report and Written Opinion for International Application No. PCT/FR2011/050417 and English translation thereof, dated May 9, 2011.
Chen Jiunn-Rong et al: "Rapid identification and susceptibility testing using the VITEK (R ) 2 system using culture fluids from positive BacT/Alert (R) blood cultures", Chinese Journal of Microbiology. Zhonghua Minguo, Lippincott Williams & Wilkins Asian, HK; vol. 41, No. 3, Jun. 1, 2008; pp. 259-264.
Lupetti A et al.: "Rapid Identification and Antimicrobial susceptibility profiling of Gram-positive cocci in blood cultures with the Vitek 2 system" European Journal of Clinical Microbiology & Infectious Diseases, Springer, Berlin, DE, vol. 29, No. 1, Nov. 10, 2009, pp. 89-95.
Lupetti A et al.: "Rapid Identification and Antimicrobial susceptibility profiling of Gram-positive cocci in blood cultures by direct inoculation into the BD Phoenix System." Clinical Microbiology and Infection: The Official Publication of the European Society of Clinical Microbiology and Infectious Diseases , Jul. 2010 Lnkd-Pubmed: 19681952, vol. 16, No. 7, Oct. 20, 2009, pp. 986-991.
Jain Sarjana et al. "Rapid detection of extended-spectrum beta-lactamase-producing Gram-negative bacilli in blood cultures", Journal of Antimicrobial Chemotherapy, Oxford Univeristy Press, GB, vol. 60, No. 3, Sep. 1, 2007, pp. 652-654.

*Primary Examiner* — Maryam Monshipouri
(74) *Attorney, Agent, or Firm* — Davidson, Davidson & Kappel LLC

(57) ABSTRACT

The present invention concerns an in vitro method for detecting an enzyme or a microorganism in a biological sample, comprising the steps of:
a1) concentrating the microorganisms present in the biological sample, optionally after a a0) culture step of the microorganisms;
b1) placing in suspension the microorganisms concentrated at step a1) in a solution containing at least one chromogenic or fluorogenic substrate capable of releasing a chromophore or fluorophore after hydrolysis by the enzyme to be detected;
c1) detecting potential release of the chromophore or fluorophore obtained at step b1);
the release of the chromophore or fluorophore detected at step c1) indicating the presence of the enzyme to be detected.

12 Claims, No Drawings

QUICK METHOD FOR DETECTING ENZYMES AND MICROORGANISMS

This application is a U.S. national phase application of International Application No. PCT/FR2011/050417 filed Mar. 1, 2011, the disclosure of which is hereby incorporated by reference herein.

FIELD OF THE INVENTION

The present invention concerns quick methods for detecting enzymes and microorganisms.

BACKGROUND OF THE INVENTION

Methods for detecting microorganisms in a clinical sample generally comprise the following steps:

1) Optionally treating the sample to promote bacterial growth, the length of this step varying in relation to the type of sample (blood, urine, stools, cerebrospinal fluid, other puncture fluids) and in relation to the bacterial load;
2) Seeding one or more agar growth media which may or may not be selective;
3) Incubating for 18 to 48 h at 37° C.;
4) Observing the different types of colonies obtained (size, appearance, colour . . . );
5) Collecting one or more isolates of each type of colony;
6) Actual identification, if necessary using an automated system or an identification gallery;
7) Obtaining an antibiogram in parallel which requires a minimum time of 16 h, or obtaining an antibiogram consecutively which requires an additional time of 18 h to determine the profile of the microorganism with respect to antibiotics and/or antifungals.

The diagnosis of an infection by microorganisms is therefore generally long, the time notably depending on the type of sample to be analysed. This waiting time is particularly problematic if the sample to be analysed is a blood sample. If it is sought to identify the presence of microorganisms in blood, the first treatment step of the sample by blood culture which allows the detection threshold of the microorganisms to be reached, may take up to 7 days. The duration of this first treatment step cannot be reduced since it is dependent on automated systems. On the slightest sign of culture positivity, Gram staining is performed on a sample taken by aseptic puncture of the film using a sterile syringe. This direct examination will allow recognition of the morphology of the bacterial agent present in the bottle which may guide towards identification of the germ. The information is then immediately transmitted to the clinician since it may allow the start of an antibiotic treatment that has not yet been initiated or the correction of probabilistic antibiotherapy. Nevertheless, no precise characterization of the microorganism under consideration is possible at this level, and even less so a profile of particular resistance. It is therefore particularly useful to be subsequently able to identify rapidly the microorganisms present in the biological sample together with their possible resistance phenotypes so as to initiate or rectify antibiotic treatment.

Different types of microorganisms can be present in positive blood cultures. It is a fact that staphylococci (not only *Staphylococcus aureus* but also negative coagulase staphylococci) are regularly found. Gram-negative bacilli especially *Escherichia coli* (and more generally enterobacteriaceae), anaerobic bacteria of the colon, members of the groups *Klebsiella/Enterobacter, Pseudomonas aeruginosa, Proteus* spp and *Providencia* spp, have been detected for example after traumatic injury or after surgery on an already contaminated body region. The detection of *salmonella* in the blood of individuals suffering from systemic salmonellosis is not unusual. Numerous other microbial genii have been found in cultures of blood samples such as streptococci, enterococci, *Brucella, Pasteurella*, pneumococci, *Neisseria, Listeria, Clostridium*, corynebacteria, *Bacteroids*, bacteria in the hacek group but also yeasts and parasites.

Different techniques are used for precise identification of these microorganisms and their possible resistance phenotypes, but the results are generally only obtained after a relatively long period.

Samples are coated on a medium containing fresh blood and chocolate blood agar to which other media may be added depending on the results of microscopy examinations.

For each positive bottle, the following are carried out:
determining the morphology of the colonies,
oxidase and catalase testing,
biochemical and antigenic identification to identify the microorganism,
susceptibility tests, evaluation of Minimum Inhibitory Concentrations (MIC).

It has been shown that it is possible to obtain an antibiogram directly from a positive blood culture using an inoculum equivalent to 0.5 McF from the blood culture broth. A Mueller-Hinton agar is inoculated using the <<flooding>> technique. The correlation with the standard antibiogram is apparently found in 95% of cases. The result appears no earlier than 16 h after evidencing of the positive blood culture (Antibiotics In Laboratory Medicine, Victor Lorian, M.D. Editor, $5^{th}$ Edition; Doern et al., 1981, *Antimicrob Agents Chemother.* 20(5): 696-698. Antimicrobial Agents).

There is therefore a major need for new, more rapid methods for detecting microorganisms, and/or their possible associated resistances, in a biological sample, these methods having to maintain satisfactory susceptibility and specificity.

β-lactams represent the largest family of antibiotics on account of the large number of molecules belonging thereto, and on account of their associated pharmacological properties and spectra which allow the combating of most bacterial species. β-lactams are rightly the antibiotics that are the most prescribed in general medicine. Their spectrum of activity varies as a function of their class (penicillins or cephalosporins) and at times as a function of the molecules in each class. For example, the G and V penicillins are rather more active on Gram-positive cocci and anaerobic bacteria, whilst the spectrum of aminopenicillins extends to a few Gram-negative bacilli. The addition of a β-lactamase inhibitor also leads to observing activity on some bacteria producing these β-lactamases. Cephalosporins further extend the spectrum of activity to Gram-negative bacilli but are a little less active on Gram-positive cocci.

Among the β-lactams, cephalosporins account for the category of antibiotics that is most often prescribed. The frequent use of cephalosporins has led to the spreading of strains resistant to these molecules. These strains in particular manage to survive the pressure of cephalosporin selection through β-lactamase activity. The detection of combined resistances against $1^{st}$, $2^{nd}$ and $3^{rd}$ generation (C3G) cephalosporins in Enterobacteriaceae is becoming of major therapeutic importance. The increasing resistance of Enterobacteriaceae to antibiotics is of world concern with an increasing impact of extended spectrum β-lactamases (ESBLs), spreading in the community in particular. In 2002, less than 1% of Enterobacteriaceae strains produced an ESBL. In 2006, they represented 1 to 5% of strains.

The resistance to C3Gs whether due to ESBLs or to other β-lactamases (cephalosporinase or carbapenemase) is therefore on the increase and has become significant in particular for *Escherichia coli* and *Klebsiella pneumoniae*. The emergence of these enzymes has recently been reported in non-fermenting Gram-negative bacilli such as *Acinetobacter baumannii, Pseudomonas aeruginosa* and *Stenotrophomonas maltophilia*. It is therefore of increasingly greater importance to be able to detect these ESBLs.

The detection of ESBLs in Enterobacteriaceae is simple to perform in most cases; it is implemented by synergy between a mixture of [amoxicillin+clavulanic acid (AMC)]and a C3G (ceftazidime is the most susceptible) or aztreonam. Nonetheless, obtaining a result requires much time. The synergy test is performed by arranging discs of AMC and the chosen C3G (or aztreonam) at a distance of 30 mm away from each other, centre to centre. The detection of ESBLs on the other hand is more difficult for strains which are also hyper-productive of cephalosporinase (AmpC) such as *Enterobacter*. In this latter case, it is easier to visualize the synergy between AMC and cefepime or cefpirome. Finally, in some species such as *Proteus mirabilis, Proteus vulgaris, Proteus penneri, Morganella morganii, Providencia stuartii* and *Providencia rettgeri*, ESBLs are weakly expressed and are therefore even more difficult to detect. In these cases, the synergy test is optimized by placing the discs at a distance of 40-45 mm, instead of 30 mm, following CA-SFM recommendations (*Comité de l'antibiogramme de la Société française de microbiologie*) in 2007. Automated bacteriological systems for identification and antibiograms are increasingly more used (Mini-Api® marketed by bioMérieux Clinical Diagnostics, Phoenix® marketed by BD Diagnostics, MicroScan® marketed by Siemens, Vitek®, Vitek-2® and Vitek Compact® marketed by bioMérieux). In general, these automated systems detect ESBLs relatively well in strains which do not usually hyper-produce cephalosporinases (*E. coli, K. pneumoniae, K. oxytoca*). For the other species (*Enterobacter, Citrobacter, Serratia*, etc.), their susceptibility and especially their specificity are not quite as good as those of manual methods. Additional tests prove to be necessary.

The detection of strains resistant to C3Gs may therefore be easy for some resistances related to some species, but in general no procedure has 100% sensitivity or allows a rapid result to be obtained.

Numerous improvements have been proposed to accelerate the process of detecting and identifying microorganisms present in blood cultures in particular. First, the improvements in culture media and growth techniques have reduced culture times. The latest generation of automated machines even allows the detection of small bacterial growth. Independently of conventional techniques, when growth is detected by an automated system, it is also possible to perform direct identification of bacteria by molecular biology (amplification and sequencing, FISH, DNA chips or specific probes . . . ). Nonetheless, most of these systems are usually not open systems and only allow the detection of one or of a small number of specific microorganisms. In addition, they possibly may not provide information on susceptibility or presumed resistance against an antibiotic. Also, these methods are efficient but expensive and/or require highly qualified laboratory technicians.

Attempts to accelerate more specific detection of microorganisms resistant to a family of antibiotics have been described. For example, Weinbren and Borthwick (Weinbren and Borthwick, 2005, *J. Antimicrob. Chemother.* 55:131-132) have described a method for the non-chromogenic detection of ESBL-producing microorganisms, in a blood culture whereby a sample of blood culture is taken and transferred onto an agar medium, discs of cefpodoxime and cefpodoxime-clavulanate then being applied to the medium. Nevertheless, this culture step on an agar medium requires an additional minimum time wait of 3.5 h to 6 h before it is possible to obtain initial results after the completion of blood culture treatment.

Navon-Venezia et al. (Navon-Venezia et al., 2005, *J. Clin. Microb.* 43:439-441) have described a method for detecting ESBL-producing bacteria from positive blood cultures consisting of taking a sample of blood culture broth and seeding it directly onto a Mueller-Hinton medium containing discs of cefpodoxime and cefpodoxime+clavulanate, without including an isolation step on agar medium. No chromogenic agent is used in this method which necessitates a culture step of 16 h to 18 h following the recommendations of the American reference work CLSI/NCCLS (Clinical and Laboratory Standards Institute/National Committee on Clinical Laboratory Standards).

Chapin and Musgnug (2003) (Chapin and Musgnug, 2003, *J. Clin Microb.* 41:4751-4754) have described a direct method for testing susceptibility to antimicrobials on positive blood cultures consisting of centrifuging 10 ml of inoculated blood culture in a serum separating tube containing a gel. The microorganisms remaining on the surface of the gel are then collected and replaced in suspension to inoculate microplates containing different dilutions of specific antibiotics. The result is only obtained however 18 to 24 h after inoculation.

Chen et al. (2008) (Chen et al., 2008, *J. Microbiol. Immunol. Infect.* 41:259-264) have described a method for identifying the susceptibility of microorganisms to a group of antibiotics using positive blood cultures which entails taking a sample of positive blood culture, removing the red blood cells by lysis and centrifugation, placing in suspension the bacterial residue in a saline solution and testing using a Vitek-2® system or AST (antimicrobial susceptibility testing). It is nevertheless necessary to wait between 2 h30 and 16 h15 after loading the Vitek-2® or AST system before it is possible to observe initial results.

The team Jain et al. (Jain et al., 2007, *J. Antimicrob. Chemother.* 60:652-654) has also described a relatively rapid method for detecting extended spectrum β-lactamases (ESBLs) by colour change of a supernatant of blood culture broth after centrifugation. On account of haemolysis problems interfering with the change in colour of the chromogenic agent, the authors proposed the prior conducting of a sub-culture in a fresh medium, thereby lengthening the time of the test method.

These techniques whereby resistant microorganisms are detected after a sub-culture step therefore remain relatively lengthy techniques.

SUMMARY OF THE INVENTION

The inventors have developed a method for quicker detection allowing the detection of specific resistance phenotypes such as those conferred on Gram-negative bacteria against $3^{rd}$ generation cephalosporins, that is performed directly on the clinical sample or after a sub-culture step but without including an isolate selection step on agar medium, and using a chromogenic or fluorogenic substrate.

The present invention concerns an in vitro detection method for detecting an enzyme of a microorganism from a biological sample, comprising the steps of:

a1) concentrating the microorganisms present in the biological sample, optionally after a a0) culture step of the microorganisms;

b1) placing in suspension the microorganisms concentrated at step a1) in a solution containing at least one chromogenic of fluorogenic substrate capable of releasing a chromophore or fluorophore after hydrolysis by the enzyme to be detected;

c1) detecting potential release of the chromophore or fluorophore obtained at step b1);

the release of the chromophore or fluorophore detected a step c1) indicating the presence of the enzyme to be detected.

The present invention also concerns a method for the in vitro preparation of a blood culture sample containing microorganisms, comprising the steps of:

A) lysing or agglutinating the red blood cells present in the blood culture sample without lysing the microorganisms present in the blood culture sample, B) separating the microorganisms present in the blood culture sample from the red blood cells lysed or agglutinated at step A), and C) optionally washing the microorganisms of the blood culture sample separated at step B).

The present invention additionally concerns an in vitro detection method for detecting microorganisms in a biological sample using the above enzyme detection method.

DETAILED DESCRIPTION OF THE INVENTION

Within the context of the invention a <<biological sample>> refers to a substance of biological origin. Preferably, the biological sample is a sample of biological fluid. Examples of biological samples include but are not limited to blood, and the components thereof, urine, stools, cerebrospinal fluid or other puncture fluids. Preferably, the biological sample of the invention is selected from the group formed by a blood sample and a urine sample.

Enzymes

Within the context of the invention, the expression <<enzyme of a microorganism>> refers to a macromolecule of protein type expressed by a microorganism and which is characterized by its catalytic activity governing specific biochemical reactions inside the microorganism or outside the microorganism when this enzyme is secreted by the microorganism.

Preferably the enzyme of the invention is chosen from the group formed by glycosidases, esterases, phosphatases, β-lactamases, in particular penicillinases, cephalosporinases, carbenicillinases, oxacillinases, carbapenemases, metallo-β-lactamases and extended spectrum β-lactamases. More preferably, the enzyme of the invention is chosen from the group formed by extended spectrum β-lactamases, cephalosporinases, carbapenemases, glycosidases and esterases. Further preferably, the enzyme of the invention is chosen from the group formed by extended spectrum β-lactamases, cephalosporinases and carbapenemases. Preferably, the enzyme is an enzyme capable of hydrolysing 3rd generation cephalosporins.

By "glycosidase" is meant herein an enzyme from the group of hydrolases acting on the glycosidic bond of oligosides and glycosides. As is well known to persons skilled in the art, the specificity of a glycosidase is a function of the type of sugar linked by a glycosidic bond. Under the nomenclature of enzymes, glycosidases belong to class 3 (corresponding to hydrolases), sub-class 2 (code EC3.2). Glycosidases particularly comprise glucosidases, xylanases, galactosidases, lactases, amylases, chitinases, fructosidases, maltases, neuraminidases, invertases, hyaluronidases and lysozymes.

More particularly, glycosidases are chosen from the group formed by N-acetyl-β-galactosaminidase, N-acetyl-β-glucosaminidase, α-amylase, α-arabinofuranosidase, α-arabinosidase, β-cellobiosidase, β-chitobiosidase, α-fucosidase, β-fucosidase, α-galactosidase, β-galactosidase, α-glucosidase, β-glucosidase, β-glucuronidase, α-maltosidase, β-maltosidase, α-mannosidase, β-mannosidase and β-xylosidase.

By "esterase" is meant herein an enzyme from the group of hydrolases splitting esters into an acid and an alcohol. As is well known to persons skilled in the art, esterases differ according to their substrate specificity, their protein structure and their biological function. Under the nomenclature of enzymes, esterases belong to class 3 (corresponding to hydrolases), sub-class 1 (code EC3.1). Esterases particularly comprise triphosphoric monoester hydrolases, sulfatases, diphosphoric monoester hydrolases, phosphoric triester hydrolases, exodeoxyribonucleases, exoribonucleases, exonucleases, deoxyribonucleases, ribonucleases, endodeoxyribonucleases and endoribonucleases.

By "phosphatase" is meant herein an enzyme removing a phosphate group from a simple molecule or from a biological macromolecule, by hydrolysing the monoesters of phosphoric acid to a phosphate ion and a molecule having a free hydroxyl group. Under the nomenclature of enzymes, phosphatases belong to class 3 (corresponding to the hydrolases), sub-class 1.3 (code EC3.1.3). As is well known to persons skilled in the art, phosphatases differ according to their substrate specificity. Phosphatases particularly comprise tyrosine phosphatases, serine/threonine phosphatases, phosphatases having double specificity, histidine phosphatases and lipid phosphatases.

By "β-lactamase" is meant herein an enzyme which hydrolyses β-lactams breaking open the β-lactam ring with the production of inactive derivatives. β-lactamases are generally secreted within the outer medium in Gram-positive bacteria, and within the periplasmic space in Gram-negative bacteria. They group together inter alia cephalosporinases, extended spectrum β-lactamases and carbapenemases. β-lactamases are divided into two main classifications:

the Bush classification determined in 1989, and updated in 1995 and again in 2009, classifies β-lactamases in relation to their preferred substrate from among penicillin, oxacillin, carbenicillin, cefaloridine, cefotaxime and imipenem, and in relation to their susceptibility to clavulanic aicd, a β-lactamase inhibitor;

the Ambler classification proposed in 1980 is based on the protein sequence of β-lactamases. It is broken down into four classes of enzymes: A, B, C and D. The β-lactamases in classes A, C and D have a serine at the active site which forms a transient covalent bond with β-lactam, leading to opening of the β-lactam ring. These β-lactamases are also called serine β-lactamases. Class B groups together metallo-enzymes requiring a zinc ion to hydrolyse the β-lactam ring.

β-lactamases are numerous and diversified in relation to the properties thereof. They are responsible for resistance to β-lactams such as penicillins, cephalosporins, monobactams, cephamycins, and carbapenems. They inactivate these antibiotics via hydrolysis of the β-lactam ring. Among the β-lactamases, β-lactamase TEM-1 is most widespread in the different bacterial species. It hydrolyses penicillins most efficiently, but not $3^{rd}$ generation cephalosporins, and it is susceptible to inhibition by clavulanic acid. Bacteria producing β-lactamases in this category can therefore easily be treated with $3^{rd}$ generation cephalosporins (C3G). On the other hand, ESBLs, some cephalosporinases and carbapenemases, when produced by bacteria, make them resistant to 3$^{rd}$ generation cephalosporins (C3GR).

The amino acid sequences of β-lactamases are very close to each other within one same family. The substitution of a small number of amino acids was therefore sufficient to enable β-lactamases of type TEM-1, initially inactive, to hydrolyse cephalosporins (β-lactamases of ESBL type for example), or to become resistant to the inhibitors.

Table 1 below describes the properties of the different types of β-lactamases, in particular of cephalosporinases, extended spectrum β-lactamases and carbapenemases.

TABLE 1

A summary, non-exhaustive table describing the properties of major β-lactamases conferring (C3GR) or not conferring C3G resistance

| | Examples | Inhibited by clavulanate | Molecular class (Ambler) | C3GR |
|---|---|---|---|---|
| broad spectrum β-lactamase (penicillinases) | TEM-1, TEM-2, SHV-1 | +++ | A | No |
| | OXA (OXA-1) family | + | D | No |
| extended spectrum β-lactamase (ESBL) | TEM, SHV, CTX-M families | ++++ | A | Yes |
| | OXA (OXA-11, -14, -15, -16, -17) family | + | D | Yes |
| cephalosporinases or AmpC | Chromosomics | 0 | C | No |
| | Hyper-produced Plasmidic: ACC-1; CMY family, DHA-1 | 0 | C | Yes |
| carbapenemases | IMP, VIM families (metallo-β-lactamases) | 0 | B | Yes |
| | KPC family | +++ | A | Yes |
| | OXA (OXA 23-27, OXA-40, OXA-48) family | + | D | Yes |

Microorganisms

By "microorganism" is meant herein a living organism having an eukaryote or prokaryote cell structure, or which is akaryotic, and is characterized in that it is unicellular, microscopic or ultramicrosopic in size and having metabolic and reproductive potential. The microorganisms of the invention particularly comprise bacteria in particular Gram-negative bacteria and Gram-positive bacteria, and fungi in particular yeasts (e.g. of *Candida* genus). More specifically, they may be a bacterium chosen from the group formed by:

Enterobacteriaceae such as strains of genus *Klebsiella*, in particular *Klebsiella pneumoniae* and *Klebsiella oxytoca*; the strains of genus *Escherichia*, in particular *Escherichia coli*; the strains of genus *Enterobacter*, in particular *Enterobacter cloacae, Enterobacter asburiae* and *Enterobacter aerogenes*; the strains of genus *Citrobacter*, in particular *Citrobacter freundii* and *Citrobacter koseri*; the strains of genus *Proteus*, in particular *Proteus mirabilis, Proteus vulgaris* and *Proteus rettgeri*; the strains of genus *Serratia*, in particular *Serratia marcescens*; the strains of genus *Salmonella*, the strains of genus *Providencia*, the strains of genus *Shigella* and the strains of genus *Kluyvera, Morganella morganii* and *Hafnia alvei;* non-fermenting Gram-negative bacilli such as the strains of genus *Acinetobacter*, in particular *Acinetobacter baumannii*; the strains of genus *Pseudomonas*, in particular *Pseudomonas aeruginosa*, the strains of genus *Stenotrophomonas*, and the strains of genus *Burkholderia;* anaerobic Gram-negative bacteria such as *Bacteroides fragilis;*

Gram-negative coccobacilli or cocci such as *Haemophilus influenzae, Bordetella* and *Neisseria* spp;

Gram-positive bacilli or cocci such as the strains of genus *Lactobacillus*; the strains of genus *Enterococcus*; the strains of genus *Streptococcus*; the strains of genus *Staphylococcus*, in particular the strains of *Staphylococcus aureus* whether or not resistant to meticillin; the strains of genus *Listeria*; and the strains of genus *Clostridium*.

Preferably, the microorganisms of the invention are chosen from the group formed by microorganisms carrying or which may acquire resistance to 3$^{rd}$ generation cephalosporins. In particular, the microorganisms of the invention are chosen from the group formed by *Klebsiella pneumoniae, Escherichia coli, Proteus mirabilis, Proteus rettgeri, Proteus vulgaris, Enterobacter cloacae, Enterobacter aerogenes, Klebsiella oxytoca, Salmonella* spp., *Pseudomonas aeruginosa, Acinetobacter baumannii, Stenotrophomonas maltophilia, Serratia marcescens, Citrobacter freundii, Citrobacter koseri, Morganella morganii*, and *Providencia* sp.

Further preferably, the microorganisms of the invention are microorganisms resistant to 3$^{rd}$ generation cephalosporins.

Preferably, when the microorganism of the invention is resistant to 3$^{rd}$ generation cephalosporins, and hence in general is also resistant to 1$^{st}$ and 2$^{nd}$ generation cephalosporins, and to penicillins, the enzyme such as defined above is chosen from the group formed by extended spectrum β-lactamases, cephalosporinases and carbapenemases.

Preferably, when the microorganism of the invention is resistant to 3$^{rd}$ generation cephalosporins, the enzyme is capable of hydrolysing the 3$^{rd}$ generation cephalosporins. Most preferably, when the microorganism of the invention is resistant to 3$^{rd}$ generation cephalosporins, the enzyme of the invention is an extended spectrum β-lactamase.

Within the context of the invention, the expression "microorganism resistant to 3$^{rd}$ generation cephalosporins" refers to microorganisms which, through the specific activity of their β-lactamase(s), continue to proliferate and/or do not die when cultured in the presence of a conventional inhibiting concentration of 3$^{rd}$ generation cephalosporins.

Preferably, the "microorganisms resistant to 3$^{rd}$ generation cephalosporins" according to the present invention are chosen from the group formed by *Klebsiella pneumoniae, Escherichia coli, Proteus mirabilis, Enterobacter cloacae, Enterobacter aerogenes, Klebsiella oxytoca, Salmonella* spp., *Pseudomonas aeruginosa, Acinetobacter* baumannii, *Stenotrophomonas maltophilia, Proteus rettgeri, Proteus vulgaris, Serratia marcescens, Citrobacter freundii, Citrobacter koseri, Morganella morganii* and *Providentia* sp.

Chromogenic or Fluorogenic Substrate

Within the context of the invention the expression "chromogenic substrate" refers to a molecule which can be split or modified by an enzyme and which comprises or is coupled to a chromophore.

By "chromophore" is meant herein a group of atoms within a molecule which is responsible for the light absorption and/or emission properties in the ultraviolet, visible or infrared range of this molecule. These properties result from the capacity to absorb the energy of photons over a range of the visible spectrum whilst the other wavelengths are transmitted or scattered.

The chromogenic substrate according to the invention can be coloured or colourless. This chromogenic substrate releases its chromophore under the action of a specific enzyme.

Within the context of the invention, the expression "fluorogenic substrate" refers to a molecule which can be split or modified by an enzyme and which comprises or is coupled to a fluorophore. This fluorogenic substrate releases its fluorophore under the action of a specific enzyme.

By "fluorophore" is meant herein a group of atoms within a molecule which is responsible for the capability of this molecule to emit fluorescence light after excitation. They are generally substances composed of several conjugated aromatic rings, or they are planar or cyclic molecules having one or more $\pi$ bonds.

Chromophores or fluorophores are well known to those skilled in the art and have routinely been used in laboratories for many years (see for example Vinazzer (1975) *Haemostasis* 4:101-9, Manafi (2000) *Int. J. Food Microbiol.* 60:205-218, Orenga et al. (2009) *J. Microbiol. Methods* 79:139-155).

The chromophore may correspond for example to a derivative of indoxyl (for example 3-indolyl-R, 5-bromo-3-indolyl-R, 5-bromo-4-chloro-3-indoxyl, 5-bromo-6-chloro-3-indoxyl or 6-chloro-3-indoxyl), to a derivative of indol (for example 7-amido-5-bromoindole), to nitrophenol or a derivative thereof (for example paranitrophenol, orthonitrophenol or orthofluorophenol), to chlorophenol or a derivative thereof (for example 4-amino-2,6-dichlorophenol), to naphthol or a derivative thereof (for example 1-naphthol or 2-naphtylamide), to 5-(4-hydroxy-3-methoxyphenylmethylene)-2-thioxothiazolidin-4-one-3-ethanoate, 3,4-cyclohexenoesculetine, 2-alizarine or 7-amido-1-pentyl-phenoxazin-3-one.

The fluorophore may correspond for example to coumarin or a derivative thereof (e.g. hydroxycoumarin, laminocoumarin, 7-amido-4-methylcoumarin, methoxycoumarin, 7-nitrocoumarin-3-carboxylic acid, phycoerythrin, fluorescein or a derivative thereof (e.g. 5-dodecanoylaminofluorescein), 4-methyl-umbelliferyl, resofurin, rhodamine, allophycocyanine, 2-(5'-chloro-2'-hydroxyphenyl)-6-chloro-4-(3H)-quinazolinone.

Within the context of the invention, the expression "chromogenic or fluorogenic substrate able to release a chromophore or fluorophore after hydrolysis by the enzyme to be detected" refers to a chromogenic or fluorogenic substrate such as defined above which, when contacted with the enzyme to which it is specific, releases the chromophore or fluorophore that it contains or to which it is coupled.

The release of the chromophore or fluorophore may be due directly or indirectly to hydrolysis of the substrate by the enzyme to be detected. For example the enzyme to be detected may hydrolyse the bond linking the substrate to the chromophore or fluorophore, thereby releasing the chromophore or fluorophore from the substrate. This direct action of the enzyme is typically observed with substrates coupled to a chromophore or fluorophore. The enzyme to be detected may also hydrolyse a domain of the substrate not involving the chromophore or fluorophore.

Therefore, detection of the release of the chromophore or fluorophore from the chromogenic or fluorogenic substrate of the invention indicates that this substrate has been hydrolysed by a specific enzyme.

Preferably, the release of the chromophore or fluorophore leads to a change in colour of the chromogenic substrate or to the emission of fluorescence by the fluorogenic substrate. As a result, the detection of the release of the chromophore or fluorophore may in particular be carried out by observing the change in colour of the chromogenic substrate or the emission of fluorescence by the fluorogenic substrate.

Preferably the chromogenic or fluorogenic substrate of the invention is a substrate or a derivative of a substrate of an enzyme such as defined above. In particular, a chromogenic or fluorogenic substrate according to the invention is a substrate or a derivative of a substrate of an enzyme chosen from the group formed by glycosidases, esterases, phosphatases, β-lactamases, in particular penicillinases, cephalosporinases, carbenicillinases, oxacillinases, carbapenemases including the metallo-β-lactamases, and extended spectrum β-lactamases. More particularly, a chromogenic or fluorogenic substrate according to the invention is a substrate or a derivative of a substrate of an enzyme chosen from the group formed by cephalosporinases, carbapenemases including the metallo-β-lactamases, and extended spectrum β-lactamases.

By "derivative of a substrate of an enzyme" is meant herein a compound derived from a substrate of an enzyme, capable of being hydrolysed by the same enzymes as the substrate from which it was produced. Preferably, a derivative of a substrate of an enzyme according to the invention is a substrate that is modified so as to contain or to be coupled to a chromophore or fluorophore.

Enzyme-specific substrates are well known to those skilled in the art. Examples of glycosidase substrates therefore comprise glycosides, uronic acids, amino sugars and acetylated sugars. Examples of esterase substrates particularly comprise butyrates, palmitates, stearates, oleates, laurates and caprylates. Examples of phosphatase substrates particularly comprise phosphate esters of alkyl alcohol, aryl phosphate esters, arylalkyl phosphate esters, enol phosphates, aryl phosphates, diaryl phosphates, inorganic pyrophosphate, organic pyrophosphate, phosphamides and thioesters. Examples of penicillinase substrates comprise penicillins and nitrocefin. Cephalosporinase substrates for example comprise nitrocefin, penicillins, $1^{st}$ generation cephalosporins and some $2^{nd}$ generation and $3^{rd}$ generation cephalosporins (such as the $3^{rd}$ generation cephalosporins defined below). Examples of carbenicillinase substrates include nitrocefin, carbenicillins, penicillins and cloxacillins. Examples of oxacillinase substrates included nitrocefin, cloxacillins, penicillins and carbenicillins. Examples of carbapenemases include penicillins, cephalosporins, carbapenemes and nitrocefin. Examples of metallo-β-lactamase substrates particularly comprise nitrocefin, penicillins, cephalosporins and carbapenemes. Examples of extended spectrum β-lactamase substrates include nitrocefin, penicillins and cephalosporins, in particular $3^{rd}$ generation cephalosporins such as defined below.

In one preferred embodiment, when the enzyme to be detected is chosen from the group formed by extended spectrum β-lactamases, cephalosporinases and carbapenemases, the chromogenic or fluorogenic substrate comprises a β-lactam ring.

By "β-lactam ring" is meant herein a cyclic heteroatomic structure consisting of three carbon atoms and one nitrogen atom. Preferably the β-lactam ring of the chromogenic or fluorogenic substrate of the invention is hydrolysed by the enzyme to be detected.

Further advantageously when the enzyme to be detected is chosen from the group formed by extended spectrum β-lactamases, cephalosporinases and carbapenemases, the chromogenic or fluorogenic substrate of the invention is a derivative of β-lactam.

Par "β-lactam" is meant herein an antibiotic containing a β-lactam ring in its molecular structure. As is well known to those skilled in the art, β-lactams encompass for example derivatives of penicillin, cephalosporins, monobactams and carbapenemes.

Further preferably, when the enzyme to be detected is chosen from the group formed by extended spectrum β-lactamases, cephalosporinases and carbapenemases, the chromogenic or fluorogenic substrate of the invention is a derivative of cephalosporin.

By "derivative of cephalosporin" is meant herein a molecule composed firstly of a group derived from a cephalosporin, or part of a cephalosporin, capable of being hydrolysed by a β-lactamase, and secondly of a chromophore of fluorophore group. Preferably the derivative of cephalosporin according to the invention is a cephalosporin modified so as to contain or be coupled to a chromophore.

Cephalosporins are usually classified into cephalosporins of first, second, third or fourth generation based on their spectrum of activity and their greater or lesser resistance or stability against β-lactamases. This classification is well known to persons skilled in the art (see for example Thompson (1987) *Mayo Clin Proc.* 62:821-34; Gustaferro and Steckelberg (1991) *Mayo Clin Proc.* 66:1064-73; and Barber et al. (2004) *Adv Biochem Eng Biotechnol.* 88:179-215). Examples of $1^{st}$ generation cephalosporins particularly include cephazolin, cephalothin, cephapirin, cephaloridin, cephalexin Keforal®, cephradine Zeefra® and cefadroxil Oracéfal®. Examples of $2^{nd}$ generation cephalosporins include inter alia cefamandole, cefuroxime Zinnat®, cefonicide, ceforanide, cefatrizine, cefotiam, cefprozil, loracarbef, cefotetan, cefotixin and cefaclor Alfatil®. Examples of $4^{th}$ generation cephalosporins particularly include cefepime and cefpirome.

Most preferably, the chromogenic or fluorogenic substrate of the invention is a derivative of a $3^{rd}$ generation cephalosporin.

By "derivative of a $3^{rd}$ generation cephalosporin" is meant herein a derivative of cephalosporin such as defined above capable of being hydrolysed by the same enzymes as the $3^{rd}$ generation cephalosporins. Preferably, a derivative of a $3^{rd}$ generation cephalosporin according to the invention is a $3^{rd}$ generation cephalosporin, or part of a $3^{rd}$ generation cephalosporin, modified so as to contain or to be coupled to a chromophore or a fluorophore. More preferably, the derivative of a $3^{rd}$ generation cephalosporin of the invention is a $3^{rd}$ generation cephalosporin or part of a $3^{rd}$ generation cephalosporin modified so as to contain or to be coupled to a chromophore.

The $3^{rd}$ generation cephalosporins generally include the compounds in particular whose English names are the following: Cefcapene (CAS Reference: 135889-00-8), Cefcapene Pivoxil (CAS Reference: 105889-45-0), Cefcapene Pivoxil Hydrochloride (CAS Reference: 147816-23-7), Cefcapene Pivoxil Hydrochloride Monohydrate (CAS Reference: 147816-24-8), Cefdaloxime (CAS Reference: 80195-36-4), Cefdaloxime Pivoxil, Cefdinir (CAS Reference: 91832-40-5), Cefditoren (CAS Reference: 104146-53-4), Cefditoren Sodium (CAS Reference: 104146-53-4), Cefditoren Pivoxil (CAS Reference: 117467-28-4), Cefetamet Pivoxil Hydrochloride, Cefetamet Pivoxyl (CAS Reference: 65243-33-6), Cefetamet (CAS Reference: 65052-63-3), Cefixime (CAS Reference: 79350-37-1), Cefixime Trihydrate, Cefinenoxime Hydrochloride (CAS Reference: 75738-58-8), Cefinenoxime (CAS Reference: 65085-01-0), Cefodizime Sodium (CAS Reference: 86329-79-5), Cefodizime (CAS Reference: 69739-16-8), Cefoperazone Sodium (CAS Reference: 62893-20-3), Cefoperazone A, Cefoperazone (CAS Reference: 62893-19-0), Cefotaxime Sodium (CAS Reference: 64485-93-4), Cefotaxime S-oxide, Cefotaxime (CAS Reference: 63527-52-6), Benzathine Cefotaxime, Desacetylcefotaxime, Cefpimizole Sodium, Cefpimizole, Cefpiramide Sodium (CA Reference: 74849-93-7), Cefpiramide (CAS Reference: 70797-11-4), Cefpodoxime Proxetil (CAS Reference: 87239-81-4), Cefpodoxime (CAS Reference: 80210-62-4), Cefpodoxime Hydrate, Cefsulodin Sodium, Cefsulodin, Ceftazidime Pentahydrate (CAS Reference: 78439-06-2), Ceftazidime (CAS Reference: 72558-82-8), Cefteram, Cefteram Pivaloyloxymethyl Ester, Ceftibuten, Trans-ceftibuten, Ceftiofur, Ceftiofur Sodium (CAS Reference: 80370-57-6), Ceftiofur Hydrochloride, Ceftiofur Sodium, Desfuroylceftiofur, Ceftiolene, Ceftizoxime Alapivoxil, Ceftizoxime Sodium, Ceftizoxime, Ceftriaxone Disodium (CAS Reference: 74578-69-1), Ceftriaxone Sodium, Ceftriaxone (CAS Reference: 73384-59-5) and the salts of these compounds. The structure and IUPAC name of these compounds can be found for example on the website chemicalland21.com.

In one particular embodiment, the $3^{rd}$ generation cephalosporin is chosen from among ceftriaxone (Rocephin®), cefotaxime (Claforan®), ceftazidime (Fortum®), cefixime (Oroken®), cefpodoxime proxetil (Orelox®), cefotiam or cefotiam hexetil (Taketiam®), Cefpirome (Cefrom®), Cefepime (Axepim®), Cefsulodine (Pyocefal®), cefatamet, ceftizoxime, cefoperazone, cefsulodin, ceftibuten and the salts of these compounds.

Examples of chromogenic substrates specific to β-lactamases are well known to those skilled in the art and particularly include nitrocefin ((3-[2,4-dinitrostyryl]-7-(2-thienylacetamido)-3-cephem-4-carboxylic acid), PADAC® (Pyridinium-2-azo-p-dimethylaniline chromophore), CENTA™, HMRZ-86 (7R)-7-[2-(aminothiazol-4-yl)-(z)-2-(1-carboxy-1-methylethoxyimino)acetamido]-3-(2,4-dinitrostyryl)-3-cephem-4-carboxylic acid trifluoroacetate, E-isomer) and cefesone or S1 (3-(2,4-dinitrostyryl)-(6R,7R)-7-phenylacetamido-ceph-3-em-4-carboxylate).

Examples of fluorogenic substrates specific to β-lactamases are well known to those skilled in the art and include in particular Fluorocillin Green 495/525 and Fluorocillin Green 345/350 Live Blazer™-FRET B/G.

In one embodiment of the invention, the derivative of a $3^{rd}$ generation cephalosporin containing or coupled to a chromophore is one of the compounds described in European patent application n° 1325923. These compounds are represented by formula (I):

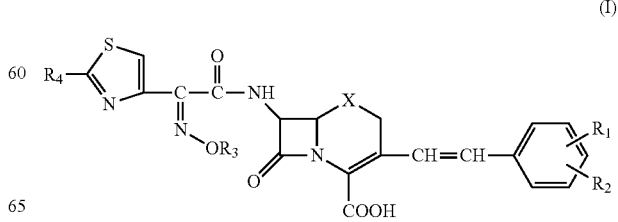

where:

$R_1$ and $R_2$ may be the same or different and each representing a hydrogen atom or a nitro or cyano group;

$R_3$ is a $C_1$-$C_6$ alkyl group, optionally substituted by a carboxyl group;

$R_4$ is a hydrogen atom or an amino group;

X is —S— or —SO—; and $R_1$ and $R_2$ cannot simultaneously represent a hydrogen atom.

Therefore the derivative of a 3rd generation cephalosporin containing or coupled to a chromophore may for example be the compound:

7-[2-(2-aminothiazol-4-yl)-2-(1-carboxy-1-methylethoxyimino)acetamido]-3-(2,4-dinitrostyryl)-3-cephem-4-carboxylic acid, 7-[2-(2-aminothiazol-4-yl)-2-(1-carboxy-1-methylethoxyimino)acetamido]-3-(2,6-dinitrostyryl)-3-cephem-4-carboxylic acid, 7-[2-(2-aminothiazol-4-yl)-2-(1-carboxy-1-methylethoxyimino)acetamido]-3-(4-nitrostyryl)-3-cephem-4-carboxylic acid, 7-[2-(2-aminothiazol-4-yl)-2-(1-carboxy-1-methylethoxyimino)acetamido]-3-(2,4-dicyanostyryl)-3-cephem-4-carboxylic acid, 7-[2-(2-aminothiazol-4-yl)-2-(1-carboxy-1-methylethoxyimino)acetamido]-3-(4-cyanostyryl)-3-cephem-4-carboxylic acid, 7-[2-(2-aminothiazol-4-yl)-2-(1-carboxy-1-methylethoxyimino)acetamido]-3-(2-cyanostyryl)-3-cephem-4-carboxylic acid, 7-[2-(1-carboxy-1-methylethoxyimino)-2-(thiazol-4-yl)acetamido]-3-(2,4-dinitrostyryl)-3-cephem-4-carboxylic acid, 1-oxide-7-[2-(2-aminothiazol-4-yl)-2-(1-carboxy-1-methylethoxy-imino)acetamido]-3-(2,4-dinitrostyryl)-3-cephem-4-carboxylic acid, 7-[2-(2-aminothiazol-4-yl)-2-methoxyiminoacetamido]-3-(4-nitrostyryl)-3-cephem-4-carboxylic acid, 7-[2-(2-aminothiazol-4-yl)-2-methoxyiminoacetamido]-3-(2,4-dicyanostyryl)-3-cephem-4-carboxylic acid, 7-[2-(2-aminothiazol-4-yl)-2-methoxyiminoacetamido]-3-(2,6-dicyanostyryl)-3-cephem-4-carboxylic acid, 7-[2-(2-aminothiazol-4-yl)-2-methoxyiminoacetamido]-3-(2-cyanostyryl)-3-cephem-4-carboxylic acid, 7-[2-(2-aminothiazol-4-yl)-2-carboxymethoxyimino-acetamido]-3-(2,4-dinitrostyryl)-3-cephem-4-carboxylic acid, 7-[2-(2-aminothiazol-4-yl)-2-carboxymethoxyimino-acetamido]-3-(2,6-dinitrostyryl)-3-cephem-4-carboxylic acid, 7-[2-(2-aminothiazol-4-yl)-2-carboxymethoxyimino-acetamido]-3-(4-nitrostyryl)-3-cephem-4-carboxylic acid, 7-[2-(2-aminothiazol-4-yl)-2-carboxymethoxyimino-acetamido]-3-(2-nitrostyryl)-3-cephem-4-carboxylic acid, 7-[2-(2-aminothiazol-4-yl)-2-carboxymethoxyimino-acetamido]-3-(2,4-dicyanostyryl)-3-cephem-4-carboxylic acid, 7-[2-(2-aminothiazol-4-yl)-2-carboxymethoxyimino-acetamido]-3-(4-cyanostyryl)-3-cephem-4-carboxylic acid, 7-[2-(2-aminothiazol-4-yl)-2-carboxymethoxyimino-acetamido]-3-(2-cyanostyryl)-3-cephem-4-carboxylic acid,

[2-carboxymethoxyimino-2-(thiazol-4-yl)acetamido]-3-(2,4-dinitrostyryl)-3-cephem-4-carboxylic acid, 1-oxide-7-[2-(2-aminothiazol-4-yl)-2-carboxymethoxy-imino-acetamido]-3-(2,4-dinitrostyryl)-3-cephem-4-carboxylic acid, or a salt thereof, such as described in European patent application n° 1325923.

In one preferred embodiment of the invention, the chromogenic substrate is the HMRZ-86 compound (7R)-7-[2-(aminothiazol-4-yl)-(z)-2-(1-carboxy-1-methylethoxyimino)acetamido]-3-(2,4-dinitrostyryl)-3-cephem-4-carboxylic acid trifluoroacetate, E-isomer) (Hanaki et al. (2004) *Journal of Antimicrobial Chemotherapy* 53:888-889). This compound is represented by the following formula (II):

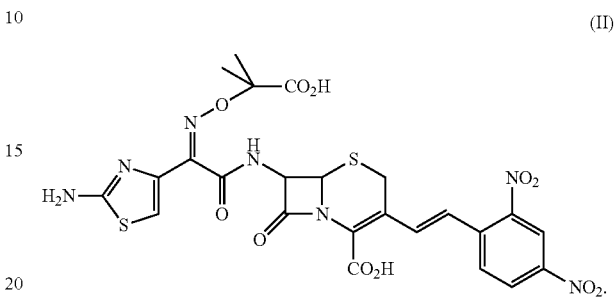

(II)

Culture Step

In some embodiments of the invention, the number of microorganisms present in the biological sample is insufficient to observe the release of the chromophore or fluorophore from the chromogenic or fluorogenic substrate of the invention. It may therefore be necessary to culture the biological sample so as to allow microorganism growth, before concentrating the microorganisms which may be present and to a obtain a number of microorganisms that is sufficient to observe the release of the chromophore or fluorophore from the chromogenic or fluorogenic substrate of the invention.

Therefore, in one preferred embodiment of the invention, the method of the invention comprises a prior a0) culture step of the microorganisms. This prior a0) culture step of the microorganisms is performed under suitable conditions to allow the growth of the microorganisms.

By "suitable conditions to allow the growth of the microorganisms" is meant herein suitable conditions of temperature, oxygenation and agitation, a suitable medium and a suitable period so that the microorganisms present in the biological sample are able to proliferate. The suitable conditions to allow the growth of the microorganisms are dependent on the microorganisms to be detected and are well known those skilled in the art. Typically, the culture step takes placed in a non-selective culture medium, preferably a liquid culture medium such as the Trypto-Casein—Soy medium (TCS) at 37° C., for a time allowing a final concentration to be obtained allowing the conducting of the test.

Preferably, when the biological sample is a blood sample; the culture step a0) is a blood culture step.

By "blood culture" is meant herein the culture of a sample of circulating blood. The conditions for blood cultures are well known to those skilled in the art and are described for example in "Hémocultures, Garnier F. and Denis F., In: Bactériologie médicale: techniques usuelles (2007) Ed. Masson 11:107-116". Typically the blood sample is placed in culture in a non-selective liquid medium such as brain-heart medium, trypticase soy medium or broth of the type Wilkins Chalgren medium, supplemented with nutrients and growth factors (for example vitamins, hemin, carbon hydrates, cystein, etc. . . . ), optionally comprising an anticoagulant such as sodium polyanethol sulfonate (SPS) and/or an antibiotic neutralizer such as cation adsorbing resins or activated charcoal. Preferably, the blood culture is performed in an automated system. Automated blood culture systems are well known to those skilled in the art and comprise Bactec® for example marketed by Becton-Dickinson and BacT/ALERT® marketed by bioMérieux. These systems ensure continuous monitoring, agitation and incubation of the blood cultures. As it grows a microorganism produces $CO_2$ inducing a drop in pH, which is detected by the automated system by means of a sensor, either via fluorescence or via reflectometry. The system alerts to any positive result by means of a visual and/or sound alarm when the concentration of microorganisms reaches a threshold concentration.

It is to be noted that the procedures of the invention are particularly advantageous for detecting the presence of an enzyme of a microorganism in a blood sample after a blood culture step. The methods of the invention effectively allow the detection of resistance in only 30 min after the blood culture step, whereas prior art methods only allowed results to be obtained after a minimum time of 16 h following after the blood culture step. This reduction in waiting time obtained with the methods of the invention is partly due to the fact that they do not contain a culture step on an agar medium.

Concentration Step

By "to concentrate" or "concentration" is meant herein the operation whereby the volume of a solution containing microorganisms is reduced by removing the aqueous part so that its microorganism content is increased. Concentration techniques are well known to persons skilled in the art and for example include centrifugation and filtration. Preferably, the concentration step comprises the centrifuging of the biological sample followed by removal of the supernatant obtained. Typically, centrifugation is conducted at a rate of about 3000 g for 2 to 10 min so as to obtain a bacterial residue. The supernatant derived from centrifugation is then removed. Filtration is performed for example through a membrane whose pore size is smaller than 1 μm (e.g. 0.45 μm). The microorganisms are then concentrated and collected on the membrane. The concentration step may also be performed in a tube with serum-separating gel such as the serum separating tube marketed by Becton Dickinson. After centrifugation, typically at 1300 g for 10 min, the microorganisms are recovered on the surface of the gel.

In addition, the concentrating of the microorganisms can be obtained by centrifuging after lysis and/or agglutination of the blood cells and/or filtration allowing the passing of the microorganisms.

The concentrated microorganisms can also be the subject of one or more washings in a buffered medium (for example a phosphate buffer).

Lysis Step

If the biological sample is a sample containing blood or red blood cells, the concentration step can be preceded by a lysis step of the red blood cells present in the blood culture. This lysis step must allow the removal of the red blood cells without the microorganisms themselves being lysed. Suitable lysis conditions for red blood cells are well known to skilled persons and for example comprise the contacting of the biological sample with a red blood cell lysis buffer (RBC buffer: 150 mM $NH_4Cl$, 10 mM $KHCO_3$, 0.01 mM EDTA) for a suitable time, for example 10 min at a suitable temperature for example between 15 and 40° C., to permit lysis of the red blood cells. Other lysis buffers which may be used herein are known to persons skilled in the art (Chen et al., (cited above); Moreau et al., 2002, *J Drug Target.* 10(2):161-73).

This lysis step can be renewed or followed by a washing step before the concentration step.

Agglutination Step

If the biological sample is a sample containing blood or red blood cells, the concentration step can be preceded by a step a') to prepare the biological sample, comprising:
  (i) agglutination of the red blood cells, and
  (ii) separation of the agglutinated red blood cells from the microorganisms present in the sample.

By "to agglutinate" or "agglutination" is meant herein the operation consisting of precipitating cells, in particular blood cells and preferably red blood cells.

Preferably, agglutination is carried out by placing the biological sample in contact with at least one agglutinating agent.

By "agglutinating agent" is meant herein a molecule inducing cell agglutination. The agglutinating agent of the invention is preferably chosen from the group formed by lectins, including concanavalin A, abrin, ricin and agglutinins such as wheat germ agglutinin and soy agglutinins; polymeric amino acids such as polylysine and polyarginine; cationic polymers such as polyethylenimine; natural or synthetic water-soluble polymers such as hexadimethirine bromide, polyvinylpyrrolidone (PVP) and polyethylene glycols (PEG); polycations such as protamine sulfate; gelatins, dextrans, fibrinogen, urea, glycerol, sodium chloride and antibodies.

Preferably the agglutinating agent used in the invention is a polyethylene glycol (PEG).

Red blood cell agglutination techniques using an agglutinating agent such as defined above are well known to persons skilled in the art and are described for example in applications WO 03/025207 and U.S. Pat. No. 4,753,776. Typically, the biological sample to be prepared is contacted with PEG at a sufficient concentration and for a sufficient time to allow the agglutination of the red blood cells present in the biological sample, for example for 1 to 30 min, preferably between 5 and 15 min.

Within the context of the invention, the step for "separation of the agglutinated red blood cells from the microorganisms present in the sample" consists of removing the agglutinated red blood cells and of retaining the microorganisms present in the treated sample. Such separation techniques are well known to persons skilled in the art and for example comprise filtration, centrifugation and/or decantation.

Filtration for example consists of contacting the biological sample and the agglutinating agent on the surface of the filter before centrifugation so as to separate the agglutinated red blood cells (which remain on the filter) from the microorganisms which are collected in the filtrate.

Decantation for example consists of contacting the biological sample and the agglutinating agent, and of removing the supernatant after agglutination and decantation.

Preferably, the separation of the agglutinated red blood cells is performed using centrifugal filters.

Step a') to prepare the biological sample such as defined above can also be preceded or followed by one or more red blood cell lysis steps of the red blood cells such as defined under the above paragraph "Lysis step".

Suspending Step

The protocols of the present invention are characterized in particular by the fact that the microorganisms, after concentration, are placed in suspension in a solution containing at least one chromogenic or fluorogenic substrate such as defined above. In this manner, the chromogenic or fluorogenic substrate is placed in contact in a solution with the concentrated microorganisms and not on a solid medium such as an agar medium.

By "placing the microorganisms in suspension" is meant herein the decreasing of bacterial aggregates by dissolving in a solution, the bacterial aggregates being derived either from natural sedimentation or from deliberate sedimentation for example by centrifugation. The end purpose of placing the microorganisms in suspension according to the present invention is to tend towards a solution in which the microorganisms are all separated from one another.

The solution in which the microorganisms are replaced in suspension contains at least one chromogenic or fluorogenic substrate such as defined above. It may also contain at least one lysing agent. The lysing agent of the invention may be a bacterial or fungal lysing agent. Preferably, the lysing agent lyses the bacterial or fungal wall without hydrolysing the chromogenic or fluorogenic substrate.

The said at least one lysing agent can be chosen from the group formed by a detergent, an enzyme which degrades the bacterial or fungal wall, an antibiotic active on the bacterial wall such as a polymyxin, and combinations thereof. Advantageously, the lysing agent can be combined with or replaced by mechanical lysing means, such as beads or ultrasound.

Within the context of the invention, a "detergent" or "surfactant" is a chemical compound having surfactant properties.

Examples of detergent are well known to skilled persons and particularly comprise those described on the Sigma website (www.sigmaaldrich.com/life-science/life-science-catalog/product-catalog.html?TablePage=20964389) and the following compounds: chenodeoxycholic acid; chenodeoxycholic sodium salt; cholic acid; dehydrocholic acid; deoxycholic acid; deoxycholic acid methyl ester; digitonin; digitoxigenin; N,N-dimethyldodecylamine oxide; sodium docusate; glycochenodeoxycholic acid sodium salt; glycocholic acid hydrate; glycocholic acid hydrate sodium salt; glycodeoxycholic acid monohydrate; glycodeoxycholic acid sodium salt; 3-sulfate disodium salt of glycolithocholic acid; glycolithocholic acid ethyl ester; sarkosyl, N-lauroyl-sarcosine sodium salt; N-lauroylsarcosine; lithium dodecyl sulfate; lugol solution; Niaproof 4 Type 4 (i.e., the sodium salt of 7-ethyl-2-methyl-4-undecyl sulfate); the sodium salt of 1-octanesulfonic acid; sodium 1-butanesulfonate; sodium 1-decanesulfonate; sodium 1-dodecanesulfonate; sodium 1-heptanesulfonate anhydrous; sodium 1-nonanesulfonate; sodium 1-propanesulfonate monohydrate; sodium 2-bromoethanesulfonate; sodium cholate hydrate; sodium choleate; sodium deoxycholate; sodium deoxycholate monohydrate; sodium dodecyl sulfate; sodium hexanesulfonate anhydrous; sodium octyl sulfate; sodium pentanesulfonate anhydrous; sodium taurocholate; sodium taurodeoxycholate; taurochenodeoxycholic acid sodium salt; taurodeoxycholic acid sodium salt hydrate; 3-sulfate taurolithocholic acid disodium salt; tauroursodeoxycholic acid sodium salt; Trizma® dodecyl sulfate (i.e., tris(hydroxymethyl)aminomethane lauryl sulfate); ursodeoxycholic acid, alkyl trimethylammonium bromide; benzalkonium chloride; benzyl dimethylhexadecylammonium chloride; benzyl dimethyltetradecylammonium chloride; benzyl dodecyldimethylammonium bromide; benzyl trimethylammonium tetrachloroiodate; cetyltrimethylammonium bromide; dimethyl dioctadecylammonium bromide; dodecyl ethyldimethylammonium bromide; dodecyl trimethylammonium bromide; ethyl hexadecyldimethylammonium bromide; Girard's T reagent; hexadecyl trimethylammonium bromide; N,N',N'-polyoxyethylene(10)-N-tallow-1,3-diaminopropane; thonzonium bromide; trimethyl (tetradecyl)ammonium bromide, BigCHAP (N,N-bis[3-(D-gluconamido)propyl]cholamide); bis(polyethylene glycol bis[imidazoyl carbonyl]); the polyoxyethylene alcohols such as Brij® 30 (polyoxyethylene(4) lauryl ether), Brij®35 (polyoxyethylene(23) lauryl ether), Brij® 35P, Brij® 52 (polyoxyethylene 2 cetyl ether), Brij® 56 (polyoxyethylene 10 cetyl ether), Brij® 58 (polyoxyethylene 20 cetyl ether), Brij® 72 (polyoxyethylene 2 stearyl ether), IBrij® 76 (polyoxyethylene 10 stearyl ether), Brij® 78 (polyoxyethylene 20 stearyl ether), Brij® 78P, Brij® 92 (polyoxyethylene 2 oleyl ether); Brij® 92V (polyoxyethylene 2 oleyl ether), Brij® 96V, Brij® 97 (polyoxyethylene 10 oleyl ether), Brij® 98 (polyoxyethylene(20) oleyl ether), Brij® 58P, and Brij® 700 (polyoxyethylene(100) stearyl ether); Cremophor® EL (polyoxyethyleneglycéroltriricinoleate 35; polyoxyl 35 castor oil); decaethylene glycol monododecyl ether; decaethylene glycol mono hexadecyl ether; decaethylene glycol mono tridecyl ether; N-decanoyl-N-methylglucamine; n-decyl alpha-D-glucopyranoside; decyl beta-D-maltopyranoside; digitonine; n-dodecanoyl-N-methylglucamide; n-dodecyl alpha-D-maltoside; n-dodecyl beta-D-maltoside; heptaethylene glycol monodecyl ether; heptaethylene glycol monododecyl ether; heptaethylene glycol monotetradecyl ether; n-hexadecyl beta-D-maltoside; hexaethylene glycol monododecyl ether; hexaethylene glycol monohexadecyl ether; hexaethylene glycol monooctadecyl ether; hexaethylene glycol monotetradecyl ether; Igepal® CA-630 (nonylphenyl-polyethyleneglycol, (octylphenoxy)polyethoxyethanol, octylphenyl-polyethylene glycol); methyl-6-O—(N-heptyl-carbamoyl)-alpha-D-glucopyranoside; nonaethylene glycol monododecyl ether; N-nonanoyl-N-methylglucamine; octaethylene glycol monodecyl ether; octaethylene glycol monododecyl ether; octaethylene glycol monohexadecyl ether; octaethylene glycol monooctadecyl ether; octaethylene glycol monotetradecyl ether; octyl-beta-D-glucopyranoside; pentaethylene glycol monodecyl ether; pentaethylene glycol monododecyl ether; pentaethylene glycol monohexadecyl ether; pentaethylene glycol monohexyl ether; pentaethylene glycol monooctadecyl ether; pentaethylene glycol monooctyl ether; polyethylene glycol diglycidyl ether; polyethylene glycol W-1 ether; polyoxyethylene 10 tridecyl ether; polyoxyethylene 100 stearate; polyoxyethylene 20 isohexadecyl ether; polyoxyethylene 20 oleyl ether; polyoxyethylene 40 stearate; polyoxyethylene 50 stearate; polyoxyethylene 8 stearate; polyoxyethylene bis(imidazolyl carbonyl); polyoxyethylene 25 propylene glycol stearate; quillaja bark saponin; esters of sorbitan fatty acid, for example Span® 20 (sorbitan monolaurate), Span® 40 (sorbitan monopalmitate), Span® 60 (sorbitan monostearate), Span® 65 (sorbitan tristearate), Span® 80 (sorbitan monooleate) and Span® 85 (sorbitan trioleate); the different alkyl ethers of polyethylene glycols such as for example Tergitol® Type 15-S-12, Tergitol® Type 15-S-30, Tergitol® Type 15-S-5, Tergitol® Type 15-S-7, Tergitol® Type 15-S-9, Tergitol® Type NP-10 (nonylphenol ethoxylate), Tergitol® Type NP-4, Tergitol® Type NP-40, Tergitol® Type NP-7, Tergitol® Type NP-9 (nonylphenol polyethylene glycol ether), Tergitol® MIN FOAM IX, Tergitol® MIN FOAM 2×, Tergitol® Type TMN-10 (polyethylene glycol trimethylnonyl ether), Tergitol® Type TMN-6 (polyethylene glycol trimethylnonyl ether), Triton® 770, Triton® CF-10 (benzyl-polyethylene glycol tert-octylphenyl ether), Triton® CF-21, Triton® CF-32, Triton® DF-12, Triton® DF-16, Triton® GR-5M, Triton® N-42, Triton® N-57, Triton® N-60, Triton® N-101 (polyethylene glycol nonyl phenyl ether; polyoxyethylene branched nonyl phenyl ether), Triton® QS-15, Triton® QS-44, Triton® RW-75 (polyethylene glycol 260 mono(hexadecyl/octadecyl)ether and 1-octadecanol), Triton® SP-135, Triton® SP-190, Triton® W-30, Triton® X-15, Triton® X-45 (polyethylene glycol 4-tert-octylphenyl ether; 4-(1,1,3,3-tetramethylbutyl) phenyl-polyethylene glycol), Triton® X-100 (t-octylphenoxypolyethoxyethanol; polyethylene glycol tert-octylphenyl ether; 4-(1,1,3,3-tetramethylbutyl)phenyl-polyethylene glycol), Triton® X-102, Triton® X-114 (polyethylene glycol tert-octylphenyl ether; (1,1,3,3-tetramethylbutyl) phenyl-polyethylene glycol), Triton® X-165, Triton® X-305, Triton® X-405 (polyoxyethylene(40) isooctylcyclohexyl ether; polyethylene glycol tert-octylphenyl ether), Triton® X-705-70, Triton® X-151, Triton® X-200, Triton® X-207, Triton® X-301, Triton® XL-80N and Triton® XQS-20; tetradecyl-beta-D-maltoside; tetraethylene glycol monodecyl ether; tetraethylene glycol monododecyl ether; tetraethylene glycol monotetradecyl ether; triethylene glycol monodecyl ether; triethylene glycol monododecyl ether; triethylene glycol monohexadecyl ether; triethylene glycol monooctyl ether; triethylene glycol monotetradecyl ether; polyoxyethylene sorbitan fatty acid esters, for example TWEEN® 20 (polyethylene glycol sorbitan monolaurate), TWEEN® 20 (polyoxyethylene (20) sorbitan monolaurate), TWEEN® 21 (polyoxyethylene (4) sorbitan monolaurate), TWEEN® 40 (polyoxyethylene (20) sorbitan monopalmitate), TWEEN® 60 (polyethylene glycol sorbitan monostearate; polyoxyethylene (20) sorbitan monostearate), TWEEN® 61 (polyoxyethylene (4) sorbitan monostearate), TWEEN® 65 (polyoxyethylene (20) sorbitan tristearate), TWEEN® 80 (polyethylene glycol sorbitan monooleate; polyoxyethylene (20) sorbitan monooleate), TWEEN® 81 (polyoxyethylene (5) sorbitan monooleate) and TWEEN® 85 (polyoxyethylene (20) sorbitan trioleate); tyloxapol; n-undecyl beta-D-glucopyranoside, CHAPS (3[(3-cholamidopropyl)dimethylammonio]-1-propanesulfonate); CHAPSO (3-[(3-cholamidopropyl)dimethylammonio]-2-hydroxy-1-propanesulfonate); N-dodecylmaltoside; alpha-dodecyl-maltoside; beta-dodecyl-maltoside; the inner salt of 3-(decyldimethylammonio)propanesulfonate (SB3-10), the inner salt of 3-(decyldimethylammonio)propanesulfonate (SB3-10), the inner salt of 3-(dodecyldimethylammonio)propanesulfonate (SB3-12), the inner salt of 3-(N,N-dimethylmyristylammonio)propanesulfonate (SB3-14), the inner salt of 3-(N,N-dimethylpalmitylammonio)propanesulfonate (SB3-16), the inner salt of 3-(N,N-dimethyloctadecylammonio)propanesulfonate (SB3-18); MEGA-8; MEGA-9; MEGA-10; methylheptylcarbamoyl glucopyranoside; N-nonanoyl N-methylglucamine; octyl-glucopyranoside; octyl-thioglucopyranoside; octyl-beta-thioglucopyranoside; 3[N,N-dimethyl(3-myristoylaminopropyl)ammonio]propanesulfonate or amidosulfobetain-14 (ASB-14); amidosulfobetain-16 (ASB-16); EMPIGEN® BB; Cymal-1, Cymal-2, Cymal-5, Cymal-6 and deoxycholic acid.

Preferably, in the methods of the invention, the detergent is chosen from the group formed by CHAPS, Tween 20, Tween 80, c7bzo, octylglucoside, octylthioglucopyranoside, ASB-14, SB3-10, sodium dodecyl sulfate, digitonin, sarkosyl and tergitol.

The lysing agent can also be an enzyme which degrades the bacterial wall such as lysozyme, lysostaphin, achromopeptidase, mutanolysin, labiase, chitinase, glucanase, glucosaminidase, muramidase, lytic transglycosylase, amidase and endopeptidase.

The lysing agent may be an agent causing the formation of pores in the bacterial wall or the cell membrane such as a polymyxin for example, in particular a polymyxin A, B, C, D, E (or colistin), F, K, M, P, S or T. Polymyxins are cyclic peptide antibiotics which act as cationic detergents and insert themselves among the phospholipids of the bacterial wall. They may also be β-lactams, glycopeptides, fosfomycin, cycloserine, bacitracin, fusidic acid or neomycin.

At step b1) for placing in suspension, the chromogenic or fluorogenic substrate can also be placed in the presence of a least one β-lactamase inhibitor. The solution in which the microorganisms are placed in suspension may therefore further comprise at least one β-lactamase inhibitor, in particular at least one β-lactamase inhibitor chosen from the group formed by a cephalosporinase inhibitor, a serine β-lactamase inhibitor, a metal chelator and a ESBL inhibitor.

Examples of β-lactamase inhibitors are well known to persons skilled in the art and particularly include cloxacillin, the syn2190 compound, aztreonam, boronic acid and derivatives thereof such as 3-aminophenyl boronic acid, phenyl boronic acid, benzo(b)thiophene-2-boronic acid, meta-carboxyphenylboronic acid; clavulanic acid, salts of clavulanic acid, tazobactam and sulbactam; dipicolinic acid (DPC), diethyldithiocarbamate (DEDTC), N,N,N',N'-tetrakis-(2-pyridylmethyl)-ethylenediamine (TPEM), ethylene diamine tetra acetic acid (EDTA), 2,3-dimercapto-1-propane sulfonic acid (DMPS) and 1,10-phenanthroline; ceftazidime, a salt of ceftazidime, cefotaxime and a salt of cefotaxime; BAL30072 siderophore monobactam, 2-amino-4-thiazolyl methoxyimino-penicillin (ATMO-penicillin); C-6-mercaptomethyl penicillinate; BRL 42715 methylidene penem; BLI-489 methylidene penem; alkylidene penems; tri- and bicyclic methylidene penems; LK-157 tricycylic carbapenem; 1-b-methylcarbapenem 225; Ro 48-1220 penam sulfone; LN-1-255 penam sulfone; sodium salt of trans-7-oxo-6-(sulfooxy)-1,6-diazabicyclo[3.2.1]octan-2-carboxamide (NXL104); the phosphonates and derivatives thereof such as the cyclic acyl phosphonates; penicillins such as JDB/LN-I-255; the sulfonic cephalosporins such as JBB/DVR-II-214. It is known that the choice of the inhibitors which can be used may depend on the type of enzyme it is desired to detect (WO2009/051838).

Preferably, the microorganisms are left in suspension in the solution comprising a chromogenic or fluorogenic substrate according to the invention at a suitable temperature and for a suitable time to allow the hydrolysis of the substrate by the enzyme and the detection of any release of the chromophore or fluorophore. Such conditions are well known to skilled persons and are a function of the chromogenic or fluorogenic substrate used. Typically, the microorganisms are left to incubate for 5 min to 2 h, at a temperature of between 15 and 42° C. The release of the chromophore or fluorophore, which is characterized by a change in colour of the chromogenic substrate or fluorescence emission by the fluorogenic substrate, can then be directly observed in solution.

The methods of the invention have the advantage of largely reducing the time after which it is possible to detect the presence of an enzyme of a microorganism in a biological sample. This saving in time is due in particular to the fact that the methods of the invention do not comprise any culture step of the microorganisms in a selective medium containing a specific antibiotic. In particular, they do not comprise any selection step or microorganism inducing step on an agar medium.

If the biological sample is a sample containing blood or red blood cells, the detection method of the invention may further comprise a step to lyse the red blood cells present in the biological sample before the suspending step as described above in the section titled "Lysis step".

Method for Preparing a Blood Culture Sample

A further subject of the present invention is a method for the in vitro preparation of a blood culture sample containing microorganisms, comprising the steps of:
- A) lysing or agglutinating the red blood cells present in the blood culture without lysing the microorganisms present in the blood culture sample,
- B) separating the microorganisms present in the blood culture sample from the red blood cells lysed or agglutinated at step A), and
- C) optionally washing the microorganisms of the blood culture sample separated at step B).

Preferably, the above preparation method allows microorganisms to be obtained on which it is possible to apply step a1) of the detection methods such as defined above.

The lysis step A) of the red blood cells can typically be implemented as indicated above under the paragraph "Lysis step", by placing the blood culture sample in contact with a lysis buffer of red blood cells, RBC lysis buffer, for a suitable time for example between 1 min and 10 min, at a suitable temperature, for example ambient temperature or at 37° C., to allow lysis of the red blood cells.

The agglutination step A) of the red blood cells can typically be implemented as indicated above under the paragraph "Agglutination step" placing the blood culture in contact with at least one agglutinating agent such as defined above.

The separation step B) to separate the microorganisms present in the blood culture sample can be implemented using any suitable technique well known to persons skilled in the art. The step to separate the microorganisms can be performed in particular by centrifugation, filtration or removing the aqueous phase, for example after decantation. Preferably the step to separate the microorganisms is implemented by centrifugation.

The optional washing step may typically be performed by re-suspending the separated microorganisms in a washing buffer, such as the RBC lysis buffer, incubating for a suitable time, at a suitable temperature and further separation of the microorganisms, for example by centrifugation.

In Vitro Detection Method of Microorganisms

As indicated above, with the in vitro methods for detecting enzymes according to the invention, the enzymes to be detected are produced by particular microorganisms. The presence of the enzyme to be detected therefore means that the microorganism producing this enzyme is present in the biological sample.

Therefore, the present invention also concerns an in vitro method for detecting microorganisms in a biological sample using the enzyme detecting method such as defined above.

In particular, one embodiment of the invention concerns an in vitro method for detecting a microorganism in a biological sample comprising the steps of:
- a1) concentrating the microorganisms present in the biological sample, optionally after a a0) culture step of the microorganisms such as defined above;
- b1) placing the microorganisms concentrated at a1) in suspension in a solution comprising at least one chromogenic or fluorogenic substrate capable of releasing a chromophore or a fluorophore after hydrolysis by an enzyme of the microorganism to be detected such as defined above;
- c1) detecting any release of the chromophore or fluorophore obtained at step b1);

the release of the chromophore or the fluorophore detected at step c1) indicating the presence of the microorganism to be detected.

The detection of the release of the chromophore or the fluorophore from the chromogenic or fluorogenic substrate according to the invention is therefore indicative of the presence of microorganisms expressing the enzyme specific to the chromogenic or fluorogenic substrate of the invention.

The following examples illustrate the invention without limiting the scope thereof.

Example 1

Detection of β-Lactamase Conferring Resistance to $3^{rd}$ Generation Cephalosporins Upon Microorganisms Producing this β-Lactamase, Directly from Urines without any Bacterial Growth Step This example shows that it is possible to identify Enterobacteriaceae resistant to $3^{rd}$ generation cephalosporins (C3G), directly from urine.

Two urines were collected from healthy volunteers (one male and one female). These urines were each separately inoculated with different loads of two strains of *Escherichia coli* (T434=resistant to C3G having major β-lactamase activity; ATCC 25922=susceptible).

Briefly, 1 ml of urine was inoculated with 1, 10 or 100 μL of a 0.5 McFarland (McF) bacterial suspension. The tubes were centrifuged at 3000 g or 6000 g optionally with washings.

To the bacterial residue obtained were added 20 μL of a solution containing 0.8 g/L of HMRZ-86 substrate and 20 μL of CHAPS at 20 g/L. After vortexing for 10 seconds the tube was left 30 min at ambient temperature.

The inventors observed a positive reaction for the strongest inoculum. A change from yellow to orange was observed with the resistant strain when its number reached $6.10^6$ cfu/mL whereas no change was visible with the susceptible strain.

Example 2

Detection of β-Lactamase Conferring Resistance to $3^{rd}$ Generation Cephalosporins Upon Microorganisms Producing this β-Lactamase, with a Bacterial Growth Step This test was performed in a microplate.

Each well contained:

50 μL of HMRZ-86 dissolved in buffered TCS medium 60 g/L (0.2 M phosphate buffer, pH 6), 40 μL of CHAPS or $H_2O$, 10 μL of a dense bacterial suspension (5 McF, $>10^8$ cfu/ml).

The microplates were observed every hour to detect any colour change.

After 3 h, for example out of a panel of 8 resistant strains and 4 susceptible strains, with 0.4 g/L of HMRZ-86 and between 10 and 20 g/L of CHAPS, and a strong inoculum, the results given in Table 2 were obtained.

TABLE 2

|  | Water | | CHAPS | |
|---|---|---|---|---|
|  | Resistant strains | Susceptible strains | Resistant strains | Susceptible strains |
| «Significant» change | 3 |  | 5 |  |
| Uncertain change | 1 |  |  |  |
| No change | 4 | 4 | 3 | 4 |

After 3 h30, in another example, out of a panel of 8 resistant strains and 4 susceptible strains using 0.4 g/L of HMRZ-86, in or not in the presence of 5 g/L CHAPS and using a strong inoculum, the results given in Table 3 were obtained.

TABLE 3

|  | With CHAPS | | Without CHAPS | |
|---|---|---|---|---|
|  | Resistant strain | Susceptible strain | Resistant strain | Susceptible strain |
| «Significant» change | 4 |  | 6 |  |
| Uncertain change | 1 | 1 |  |  |
| No change | 3 | 3 | 2 | 4 |

Therefore, the presence of CHAPS promotes the reaction if a prior bacterial growth step is conducted.

Example 3

Detection of β-Lactamase Conferring Resistance to 3$^{rd}$ Generation Cephalosporins Upon Microorganisms Producing this β-Lactamase, Directly from a Blood Culture This example shows that it is possible to identify Enterobacteriaceae resistant to 3$^{rd}$ generation cephalosporins (C3G) directly from a blood culture.

To examine the possibility of detecting strains resistant to C3Gs in blood cultures, the adopted protocol was the following (NB: variants of the protocol not leading to any variation in the results obtained are given between square brackets. They were applied to 2 strains, a susceptible strain and a resistant strain. A change in colour was observed for the resistant strain and no change was observed for the susceptible strain):

To 7.5 mL of medium from the blood culture bottle (bacTAlert; réf 259791 or 259793) were added 2.5 mL of defibrinated sheep blood. 25 µL of a 0.5 McF bacterial suspension were added. After homogenising by vortexing and incubation for 18-20 h at 37° C., 500 µL were sampled. 0.5 mL [or 1 mL] of modified red blood cell lysis solution containing NH$_4$Cl in particular but not containing EDTA (SL) were added. After homogenising by vortexing, the tube was incubated 10 min at 37° C., [or 1 min at 37° C. or 1 min at ambient temperature]. A residue collected after centrifugation at 750 g for 5 min [or 2 min] was re-suspended in 200 µL of SL and left 2 min at ambient temperature. 1 mL of 0.1 M PBS was then added. The tube was again centrifuged at 750 g for 5 min [or 2 min], and the residue was dissolved in a solution comprising 50 µL of HMRZ-86 substrate (1.2 g/L) and 50 µL of CHAPS (30 g/L). After homogenising vortexing, the tube was left to incubate for 15 min at ambient temperature. After centrifuging at 750 g for 5 min [or 2 min], the change in colour was observed.

The test was conducted on 4 strains of which 3 strains were resistant C3G (including 2 metallo-β-lactamases whose reaction was inhibited in the presence of the culture medium) and one susceptible strain.

A test was conducted on the two blood culture media (aerobic and anaerobic) over a wider panel. In the aerobic medium 17 C3G resistant strains out of 18 responded positively to the test and 6 susceptible strains out of 8 did not show any significant colour change. In the anaerobic medium, 16 C3G resistant strains out of 18 responded positively to the test and 6 out of 8 susceptible strains did not show any significant colour change.

Tests were similarly conducted using bottles of blood culture medium supplemented with whole human blood.

Different protocols were followed:

To 7.5 mL of medium derived from the blood culture bottle (bacTAlert; ref 259791 or 259793) were added 2.5 mL of whole human blood. 25 µL of a 0.5 McF bacterial suspension were added. After homogenising by vortexing, the tube was incubated 18-20 h at 37° C.

Lysis Protocol 0.5 ml of blood culture were sampled and 0.5 mL of lysis buffer was added thereto. The mixture was left in contact for 10 min then centrifuged for 2 min at 750 g. The residue was subjected twice again to the same protocol (addition of lysis buffer then centrifugation). It was then dissolved in a solution containing 50 µL of HMRZ-86 substrate (1.2 g/L) and 50 µL of CHAPS (30 g/L). After homogenising by vortexing, the tube was incubated 15 min at ambient temperature. Any change in colour was noted after centrifuging 2 min at 750 g.

Protocol for <<Agglomeration—Filtration on Centrifugal Filter>>

50 mg of PEG were deposited on a centrifugal filter of the type: <<Millipore Ultrafree MC centrifugal filter units 5 µm>>. 0.5 mL of blood culture were taken and deposited on the filter and left in contact with the PEG for 5 min. After centrifuging 5 min at 5500 g (which allowed filtration) and removal of the supernatant above the filter, the filtrate was treated with 1 mL of lysis buffer for 10 min. The tube was centrifuged 5 min at 5500 g, the supernatant was removed.

The residue was then dissolved in a solution containing 50 µL of HMRZ-86 substrate (0.8 g/L) and 50 µL of CHAPS (20 g/L). After homogenising by vortexing, the tube was incubated 15 min at ambient temperature then any change in colour was noted.

Protocol for <<Agglomeration—Decantation>>

1 ml of blood culture was taken and 200 mg PEG added thereto. The mixture was left to decant for 15 min. 500 µL of supernatant was placed in another tube. After centrifuging 5 min at 5500 g and removal of the supernatant, the residue was treated with 1 mL of lysis buffer and after 10 min it was again centrifuged for 5 min at 5500 g.

The residue was then dissolved in a solution containing 50 µL of HMRZ-86 substrate (0.8 g/L) and 50 µL of CHAPS (20 g/L). After homogenising by vortexing followed by incubation 15 min at ambient temperature, any change in colour was noted.

All these three protocols allow limiting of red colouring due to the blood culture, and rapid C3GR identification.

They were applied to a C3GR strain and a C3GS strain: the test with the C2GR strain showed bright red colouring whereas the test with the C3GS strain remained orangish-yellow.

Example 4

Detection of the Glycosidase Activity of *Candida tropicalis* (Substrate: 5-bromo 4-chloro 3-indolyl α-glucoside) of *Enterococcus faecalis* (Substrate: 5-bromo 4-chloro 3-indolyl β-glucoside) and the Esterase Activity of *Pseudomonas aeruginosa* or *Salmonella enteritidis* (Substrate: 5-bromo 4-chloro 3-indolyl butyrate), Directly from Urine Urines from healthy individuals were artificially contaminated. For this purpose, a 0.5 McF bacterial suspension (about $10^{7-8}$ cfu/ml) was prepared in physiological water. This suspension was centrifuged for 5 min at 6000 g and the supernatant was removed. The residue was then dissolved in 1 mL of urine to obtain a concentration of about $10^{7-8}$ cfu/ml urine. The contaminated urine was incubated for 15 to 30 min. It was then centrifuged for 5 min at 6000 g and the supernatant removed. The residue was dissolved in a solution containing 50 µL of chromogenic substrate 2× and 50 µL of detergent 2×. The change in colour was observed after an incubation time of 30 min at ambient temperature.

The results obtained with the test to detect glycosidase activity are given in Tables 4 and 5.

TABLE 4

| | *Candida tropicalis* ATCC 750 |
|---|---|
| Substrate | X-α-glucoside |
| Read time | 30 min |
| 0.1M phosphate buffer pH 7 (Bp) | White |
| Bp + Digitonin 0.5 g/L | Blue |
| Bp + OTG 5 g/L | Blue |

(OTG = Octyl-β-thioglucopyranoside; X = 5-bromo 4-chloro 3-indolyl).

TABLE 5

| | *Enterococcus faecalis* ATCC 29212 |
|---|---|
| Substrate | X-β-glucoside |
| Read time | 30 min at AT |
| 0.1M phosphate buffer pH 7 | Blue reflections/light blue |

The results obtained with the test for detecting the esterase activity are given in Tables 6 and 7.

TABLE 6

| | *P. aeruginosa* RDC 45 |
|---|---|
| Substrate | X-butyrate |
| Read time | 45 min at 37° C. |
| 0.1M phosphate buffer H7 (Bp) | White |
| Bp + PolyB 250 mg/L | Blue |
| Bp + CHAPS 10 g/L | White |
| Bp + CHAPS + PolyB | Blue |

(polyB = polymyxine B)

TABLE 7

| | *Salmonella enteritidis* ATCC 13076 |
|---|---|
| Substrate | X-butyrate |
| Buffer | 0.1M phosphate buffer pH 7 (Bp) |
| Read time | 1 h at AT |
| Bp + PolyB 250 mg/L | Blue reflections (BR)/light blue |

TABLE 7-continued

| | *Salmonella enteritidis* ATCC 13076 |
|---|---|
| Bp + CHAPS 10 g/L | BR |
| Bp + Tween 20 0.2% | BR |
| Bp + CHAPS + PolyB | BR/light blue |
| Bp + Tween 20 + PolyB | BR/light blue |

The influence of temperature and incubation time was tested (see Table 8).

TABLE 8

| | *P. aeruginosa* RDC45 Substrate X-butyrate Read time | | |
|---|---|---|---|
| | 1 h at AT | 45 min at 37° C. | 1 h 15 at 37° C. |
| Negative bacteria-free control in Bp (0.1M phosphate buffer pH 7) | ND | White | Blanc |
| Bp | ND | White | Blue reflectn. (BR) |
| Bp + CHAPS 10 g/L | White | White | BR |
| Bp + PolyB 250 mg/L | BR- | Light blue | Blue |
| Bp + CHAPS + PolyB | BR- | Light blue | Blue - |

ND: not determined

Example 5

Detection of β-Lactamase Conferring Resistance to $3^{rd}$ Generation Cephalosporins Upon Microorganisms Producing this β-Lactamase, Directly from Blood Cultures Positive to Gram-Negative Bacilli This example shows that it is possible to detect resistance to $3^{rd}$ generation cephalosporins (C3G) in Enterobacteriaceae or other Gram-negative bacilli such as *Pseudomonas*, directly from a blood culture.

The study was a prospective study on blood cultures positive to aerobic Gram-negative bacilli. The protocol below was conducted on the same day as the blood cultures were detected to be positive by an automated system (BacT/ALERT by Biomérieux).

Lysis Protocol 0.5 ml of blood culture was taken and 0.5 mL of lysis buffer was added thereto. The mixture was briefly vortexed then left in contact for 10 min at ambient temperature. A centrifuging step (2 min at 3000 rpm) was then performed and the supernatant removed. The residue was subjected twice to the following steps: addition of 1 mL of lysis buffer, short vortexing, 10 min wait, then centrifuging 2 min at 3000 rpm and removal of the supernatant. The residue was then dissolved in a solution containing 50 µL of HMRZ-86 substrate (1.2 g/L) and 50 µL of CHAPS (30 g/L). After homogenising by vortexing, the tube was incubated 15 min at ambient temperature. Any change in colour was noted after centrifuging 2 min at 3000 rpm.

The detected strains are given in Table 9.

TABLE 9

|  | Susceptible strains (C3GS) | Resistant strains (C3GR) |
|---|---|---|
| *Acinetobacter baumannii* | 1 | — |
| *Citrobacter freundii* | 1 | — |
| *Escherichia coli* | 10 | 3 |
| *Klebsiella oxytoca* | — | 1 |
| *Klebsiella pneumoniae* | 1 | — |
| *Pseudomonas aeruginosa* | 1 | — |
| *Yersinia enterocolitica* | 1 | — |
| TOTAL | 15 | 4 |

The results are given in Table 10.

TABLE 10

|  | Resistant strains | Susceptible strains |
|---|---|---|
| «Significant» change | 4 | 1 |
| Uncertain change | — | — |
| No change | — | 14 |

This example therefore shows that the lysis protocol allows the detection of β-lactamase conferring resistance to $3^{rd}$ generation cephalosporins upon aerobic Gram-negative bacilli producing this β-lactamase, directly from positive blood cultures. Aside from one C3GS strain which was detected as <<false positive>>, the test conducted with the C3GS strains showed pale yellow to orangish-yellow colouring, whereas the test with the C3GR strains changed from yellow to bright red.

The invention claimed is:

1. An in vitro method for detecting an enzyme of a microorganism from a biological sample, comprising the steps of:
    a1) concentrating the microorganisms present in the biological sample, optionally after a a0) culture step of the microorganisms;
    b1) placing in suspension the microorganisms concentrated at a1) in a solution comprising at least one chromogenic or fluorogenic substrate capable of releasing a chromophore or a fluorophore after hydrolysis by the enzyme to be detected;
    c1) detecting potential release of the chromophore or fluorophore obtained at step b1);
    the release of the chromophore or fluorophore detected at step c1) indicating the presence of the enzyme to be detected.

2. The method according to claim 1 wherein the biological sample is a blood sample or urine sample.

3. The method according to claim 1 wherein the culture step a0) is a blood culture step.

4. The method according to claim 1 further comprising, if the biological sample is a sample containing blood or red blood cells, a step to lyse the red blood cells present in the biological sample before step b1) for placing in suspension.

5. The method according to claim 1 further comprising, if the biological sample is a sample containing blood or red blood cells, a step to lyse the red blood cells present in the biological sample before the concentration step a1).

6. The method according to claim 1 wherein the enzyme to be detected is chosen from the group formed by extended spectrum β-lactamases, cephalosporinases, carbapenemases, glycosidases and esterases.

7. The method according to claim 1 wherein the microorganism is resistant to $3^{rd}$ generation cephalosporins, and the enzyme to be detected is chosen from the group formed by extended spectrum β-lactamases, cephalosporinases and carbapenemases.

8. The method according to claim 7 wherein at step b1) the chromogenic or fluorogenic substrate is placed in the presence of at least one β-lactamase inhibitor.

9. The method according to claim 7, wherein the chromogenic substrate is the compound HMRZ-86 ((7R)-7-[2-(aminothiazol-4-yl)-(z)-2-(1-carboxy-1-methylethoxy-imino)acetamido]-3-(2,4-dinitrostyryl)-3-cephem-4-carboxylic acid thrifluoroacetate, E-isomer) or a salt thereof.

10. The method according to claim 1 wherein the concentration step a1) comprises the centrifugation of the biological sample followed by removal of the supernatant obtained.

11. The method according to claim 1 wherein, if the biological sample is a sample containing blood or red blood cells, the microorganism concentration step a1) is preceded by a step a') to prepare the biological sample, comprising:
    (i) agglutination of the red blood cells, and
    (ii) separation of the agglutinated red blood cells from the microorganisms present in the sample.

12. An in vitro method for detecting an enzyme of a microorganism from a biological sample, comprising the steps of:
    a1) concentrating the microorganisms present in the biological sample, optionally after a a0) culture step of the microorganisms;
    b1) placing in suspension the microorganisms concentrated at a1) in a solution comprising at least one chromogenic or fluorogenic substrate capable of releasing a chromophore or a fluorophore after hydrolysis by the enzyme to be detected;
    c1) detecting potential release of the chromophore or fluorophore obtained at step b1);
    the release of the chromophore or fluorophore detected at step c1) indicating the presence of the enzyme to be detected, and
    wherein the chromogenic substrate is the compound HMRZ-86 ((7R)-7-[2-(aminothiazol-4-yl)-(z)-2-(1-carboxy-1-methylethoxyimino)acetamido]-3-(2,4-dinitrostyryl)-3-cephem-4-carboxylic acid thrifluoroacetate, E-isomer) or a salt thereof.

* * * * *